(12) United States Patent
Chien et al.

(10) Patent No.: US 9,358,511 B2
(45) Date of Patent: Jun. 7, 2016

(54) REAGENT VESSEL AND KIT THEREOF

(71) Applicant: TAIWAN ADVANCED NANOTECH INC., Taoyuan, Taoyuan County (TW)

(72) Inventors: Chien-Hsing Chien, Taoyuan (TW); Yu-Sheng Yang, Taoyuan (TW)

(73) Assignee: TAIWAN ADVANCED NANOTECH INC., Taoyuan (TW)

( * ) Notice: Subject to any disclaimer, the term of this patent is extended or adjusted under 35 U.S.C. 154(b) by 0 days.

(21) Appl. No.: 14/062,531

(22) Filed: Oct. 24, 2013

(65) Prior Publication Data

US 2014/0377149 A1 Dec. 25, 2014

(30) Foreign Application Priority Data

Jun. 21, 2013 (TW) .............................. 102211651 A

(51) Int. Cl.
*B01L 3/00* (2006.01)
*B01F 11/00* (2006.01)
*G01N 35/00* (2006.01)

(52) U.S. Cl.
CPC ......... *B01F 11/0082* (2013.01); *B01L 3/50855* (2013.01); *B01L 2200/0647* (2013.01); *B01L 2300/0858* (2013.01); *G01N 35/0098* (2013.01)

(58) Field of Classification Search
CPC ................. B01L 2300/0851; B01L 2300/0858
USPC .................................................. 422/549, 554
See application file for complete search history.

(56) References Cited

U.S. PATENT DOCUMENTS

| | | | |
|---|---|---|---|
| 5,925,319 A * | 7/1999 | Baugh | G01N 33/86 422/68.1 |
| 6,602,474 B1 * | 8/2003 | Tajima | 422/553 |
| D666,736 S * | 9/2012 | Kobayashi | D24/224 |
| 2002/0155616 A1 * | 10/2002 | Hiramatsu et al. | 436/165 |

* cited by examiner

*Primary Examiner* — Paul Hyun
(74) *Attorney, Agent, or Firm* — Birch, Stewart, Kolasch & Birch, LLP

(57) ABSTRACT

The present invention is related to a reagent vessel, comprising: at least one first tube and at least one second tube, wherein second tube has a section area of the opening greater than one of the bottom. A kit for a reagent vessel is also provided herein, comprising: the reagent vessel and a stirrer jacket, wherein the section area ratio value for the bottom of the second tube to the stirrer jacket is 1.1 to 3.5. According to the present invention, an optimum efficiency for the stirrer jacket will be achieved, and a high capacity of the operational volume will be maintained thereby.

12 Claims, 6 Drawing Sheets

REAGENT VESSEL AND KIT THEREOF

FIELD OF THE INVENTION

The invention relates to a reagent vessel and a kit thereof, more particularly, referring to a reagent vessel comprising a first tube and a second tube whose opening and bottom have a specific shape and section area ratio.

BACKGROUND OF THE INVENTION

Magnetic beads are super paramagnetic particles in micron or nano-scale, principally applied in Biotech industries, such as the purification of biomolecules (e.g. protein, enzyme, antibody, nucleic acid etc.); the preparation of test reagents for animals and plants by the binding of biomolecules and magnetic beads; the purification or concentration of specific protein active pharmaceutical ingredients (API); the tool for isolating and purifying stem cells.

For example, magnetic-bead technology in nucleic acid extraction uses a magnetic-bead reagent bearing special functional groups to adsorb specifically nucleic acids in samples with a magnetic control device having a plurality of magnetic bars which is covered outside by a stirrer jacket. The magnetic field will be provided from the magnetic control device to attract and drive magnetic beads adsorbed with nucleic acids, moving those samples to different reagent vessels, followed by stirring those ones repeatedly and quickly to be fully mixed. Finally, purified nucleic acids will be obtained after cell lysis, nucleic acid absorption, wash and elution.

However, each operating step for using magnetic-bead reagents has its special functionality, and the change of the reagent volume will be considerable thereby. Thus, optimum stirring efficiency cannot be achieved if using reagent vessels whose volume is all the same. A large amount of experimental space will be occupied, on the other hand, if the number of reagent vessels increases for the rise of stirring efficiency. In view of this, known reagent vessels should be improved.

SUMMARY OF THE INVENTION

Considering the above-mentioned deficiencies, a reagent vessel is provided herein to be concerned about both optimum efficiency and operational volume, and be applied widely in various reagents. The reagent vessel comprises:

at least one first tube, and at least one second tube arranged adjacent to the first tube, wherein the second tube further comprises:

a bottom section, comprising a bottom with a bottom section area;

an opening section, comprising an opening with an opening section area, wherein the opening section area is greater than the bottom section area, and a section area ratio of the bottom section area to the opening section area is about 1:1 to about 1:3.5; and a connecting section, being located between the bottom section and the opening section and having a pipe wall which vertically has an inclined angle less than 50°.

In one embodiment, the bottom section area is in the shape of a circle, but not limited to this, such that the bottom section area will be minimized inclinedly. One skilled in the art can optionally select any shape to reduce the bottom section area as needed.

In another embodiment, the opening section area is in the shape of a square, but not limited to this shape, such that the opening section area will be maximized inclinedly. One skilled in the art can optionally select any shape to increase the opening section area as needed.

Preferably, the section area ratio is about 1:3.0.

In another preferable embodiment, the inclined angle is less than 45.

In one embodiment, the first tube or the second tube is used for containing magnetic beads, and at least one sample or reagent. The sample or reagent may include, but not limiting to, bio-sampling samples, clinical samples, isolating reagents (e.g. organic solvent, cell lysis buffer, and enzyme solution, etc.), and reagents for the magnetic beads or extraction (e.g. various buffers).

In one embodiment, a stirrer jacket is further contained in the second tube for stirring the magnetic beads and at least one sample or reagent. As the specific shape design to the opening and the bottom, the capacity from the opening section to the connecting section will increase. Also, according to the specific section area ratio, the bottom section area and the opening section will be designed to control the stirring efficiency of the bottom section and raise the stirring effect of the stirrer jacket. The operating process, such as cell lysis or target adsorption, will thus be facilitated.

In one embodiment, the reagent vessel may comprise a plurality of first tubes. In one embodiment, the first tubes are arranged adjacently. That is, these first tubes will provide multiple isolated compartments for kinds of independent reactions of samples, reagents or enzymes during all operating steps for magnetic beads.

In one embodiment, the reagent vessel may comprise a plurality of second tubes to increase the stirring efficiency and enlarge the operational volume. In one embodiment, the second tubes may be arranged adjacently.

In one embodiment, the reagent vessel may further comprise a base comprising at least one containing tank for containing the reagent vessel.

In one embodiment, the base may comprise a plurality of containing tanks arranged side by side to reach maximum operating flux per unit area.

In one embodiment, the number of containing tanks is corresponding to the number of the reagent vessels.

The present invention also provides a kit for a reagent vessel, comprising:

at least one stirrer jacket with a stirrer jacket section area; and the above-mentioned reagent vessel, wherein the second tube has a section area ratio value of the bottom section area to the stirrer jacket area being about 1.1 to about 3.5.

In one embodiment, the section area ratio value may be about 1.1 to 2.5. The optimum efficiency will be maintained by the adjustment of the section area ratio value to about 1.1 to about 3.5, preferably, about 1.1 to about 2.5 to maintain optimum stirring efficiency.

DETAILED DESCRIPTION OF THE PREFERRED EMBODIMENTS

Preferred embodiments of the present invention will be described below in more detail with reference to the accompanying drawings. The present invention may, however, be embodied in different forms and should not be constructed as limited to the embodiments set forth herein. Other objectives, advantages, and novel features of the invention will become more apparent from the following detailed description when taken in conjunction with the accompanying drawings.

As described herein, the term "section area ratio" refers to a relationship of section area between (or among) different parts in the reagent vessel. Here, the section area ratio of numbers A to B can be expressed as "A:B". Another related term "section area ratio value" refers to the calculated result of the "section area ratio". For example, the section area ratio value will be 1.5 if the section area ratio is 1.5:1.

Figure 1:
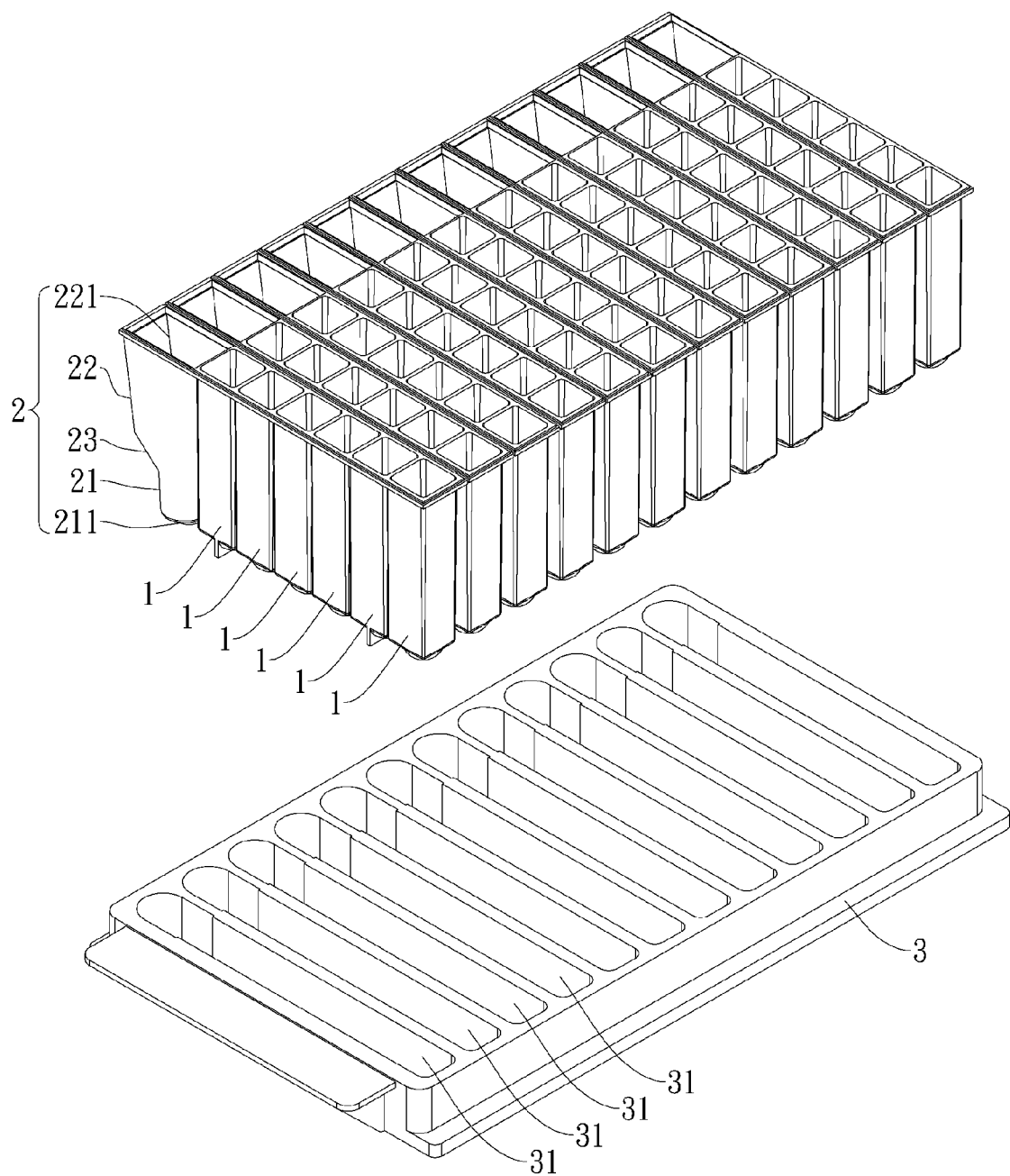
FIG. 1 illustrates an exploded pictorial drawing of a reagent vessel according to one embodiment of the present invention.
Figure 2:
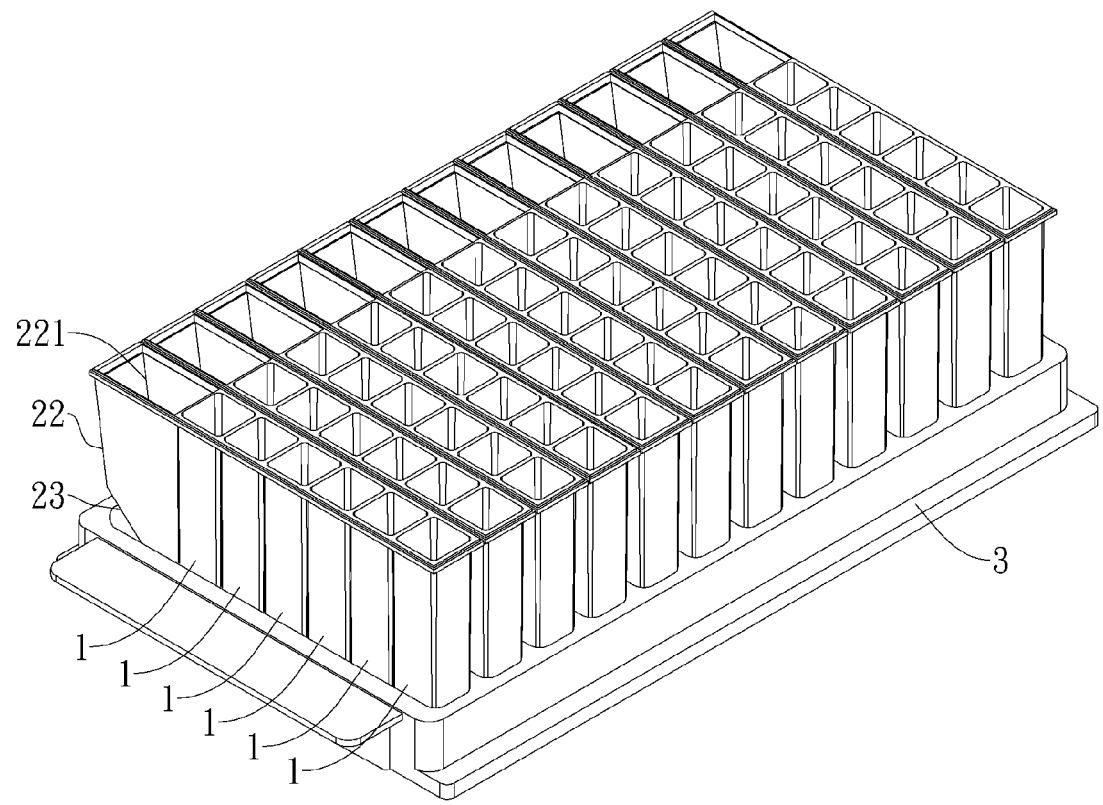
FIG. 2 illustrates a pictorial drawing of a reagent vessel according to one embodiment of the present invention.

An example of the present invention is shown in the exploded pictorial drawing of FIG. 1 and the pictorial drawing of FIG. 2, providing a reagent vessel comprising: first tubes 1, a second tube 2 and a base 3, which are detailed as follows.

The first tubes 1 are plural and arranged adjacently to provide multiple isolated compartments for kinds of independent reactions of reagents or enzymes during all operating steps for the magnetic beads. First tubes 1 are used for containing magnetic beads, and at least one sample or reagent, such as sample materials as needed in nucleic acid isolation or extraction. Examples may include, but not limiting to, biosampling samples, clinical samples, isolating reagents (e.g. organic solvent, cell lysis buffer, and enzyme solution, etc.), reagents for magnetic beads or extraction (e.g. various buffers).

The second tube 2 is arranged adjacent to the first tubes. As shown in FIG. 5 to FIG. 8, the second tube 2 is used for accommodating a stirrer jacket 4 to mix magnetic beads and at least one sample or reagent. The second tube 2 comprises:

a bottom section 21, comprising a bottom 211 with a circle section area.

an opening section 22, comprising an opening 221 with a square section area. And, the opening 221 section area is greater than the bottom 211 section area. In one example, a section ratio of the bottom section 211 area to the opening 221 section one of about 1:1 to about 1:3.5. In a preferred example, the section area ratio is about 1:3.0.

Figure 3:
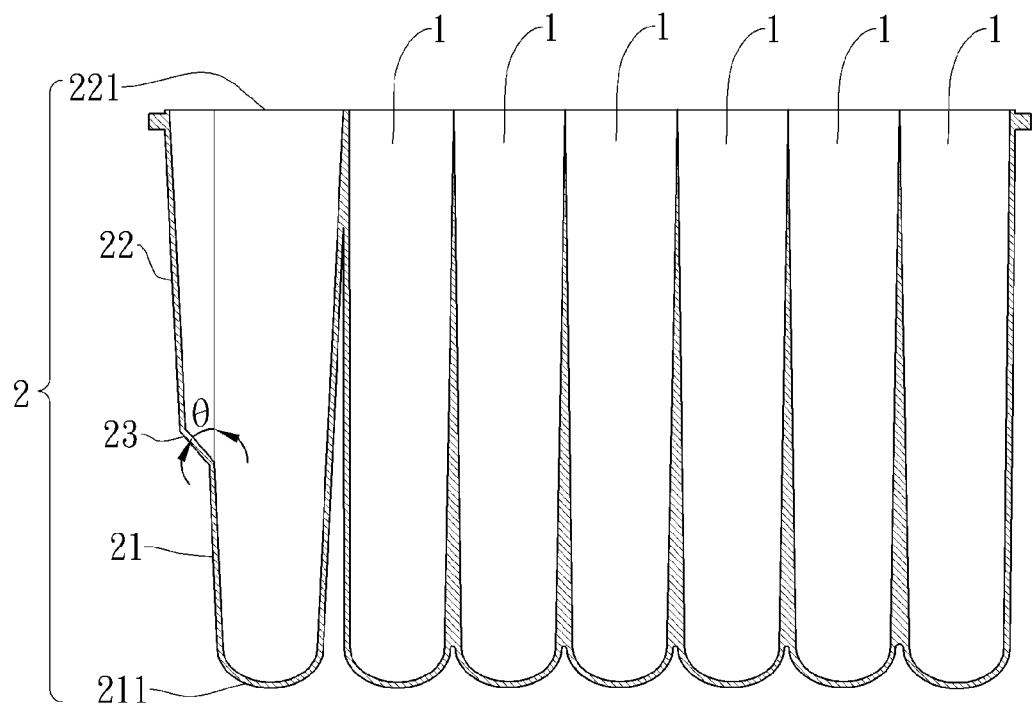
FIG. 3 illustrates a front view of a reagent vessel according to one embodiment of the present invention.
Figure 7:
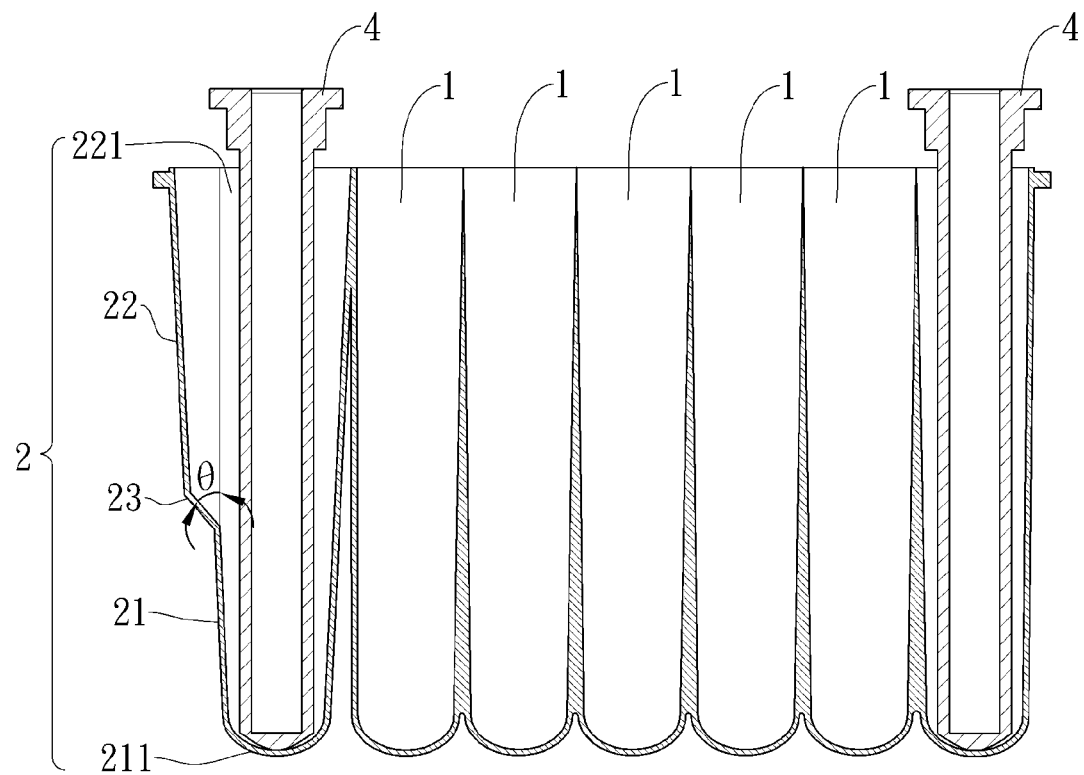
FIG. 7 illustrates a front view of a kit for a reagent vessel according to one embodiment of the present invention.

A connecting section 23, being located between the bottom section 21 and the opening section 22 and having a pipe wall which vertically has an inclined angle θ less than 50° as shown in FIG. 3 and FIG. 7.

Figure 4:
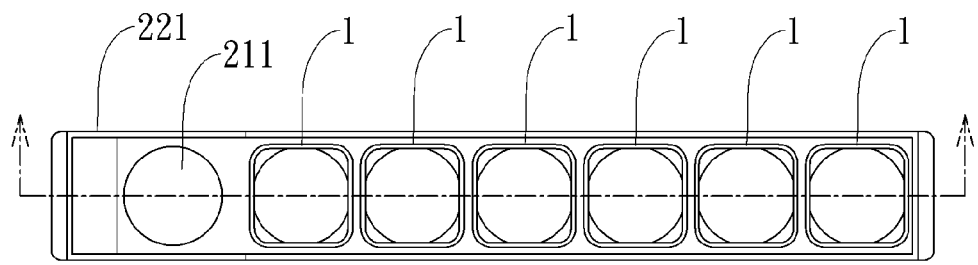
FIG. 4 illustrates a top view of a reagent vessel according to one embodiment of the present invention.

The difference of the section area of the first tubes 1 and the second tube 2 was obviously shown in FIG. 3 and FIG. 4. According to the specific shape design of the square opening and the circle bottom and their size difference, the capacity of the opening section 22 and the connecting section 23 will maximize to maintain a high operating volume. On the other hand, consideration will be also given to the stirring efficiency to minimize the capacity of the bottom section 21, so that the contained magnetic beads, samples or reagents will be concentrated to reach optimum efficiency.

Figure 8:
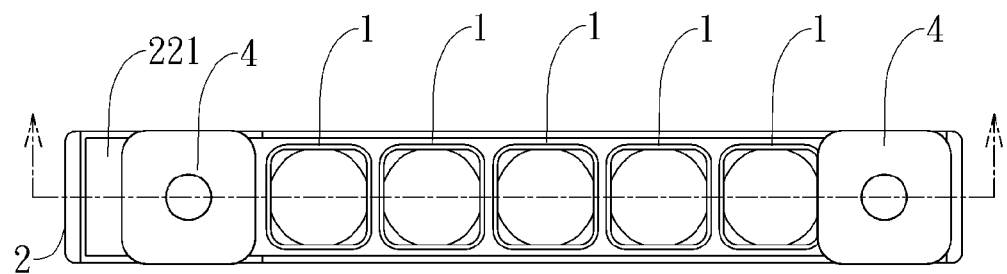
FIG. 8 illustrates a top view of a kit for a reagent vessel according to one embodiment of the present invention.

In addition, referring to the front view of FIG. 7 and the top view of FIG. 8, the bottom 211 of the second tube 2 and stirrer jacket 4 can be designed according to a section area ratio value of about 1.1 to about 3.5. In a preferred example, the second tube 2 has a section area ratio value of the bottom 211 to the stirrer jacket 4 being about 1.1 to about 2.5. The optimization of the relationship to the section area between both parts will reach optimum stirring efficiency and facilitate the operating process, such as cell lysis or target adsorption.

A base 3 is also provided in this example, comprising: a plurality of containing tanks 31 arranged side by side, and the number of containing tanks 31 is corresponding to the number of the reagent vessels, such that maximum operating flux per unit area will reach. Also, the base 3 can be designed to move simultaneously with the reagent vessel to increase the operating convenience.

Figure 5:
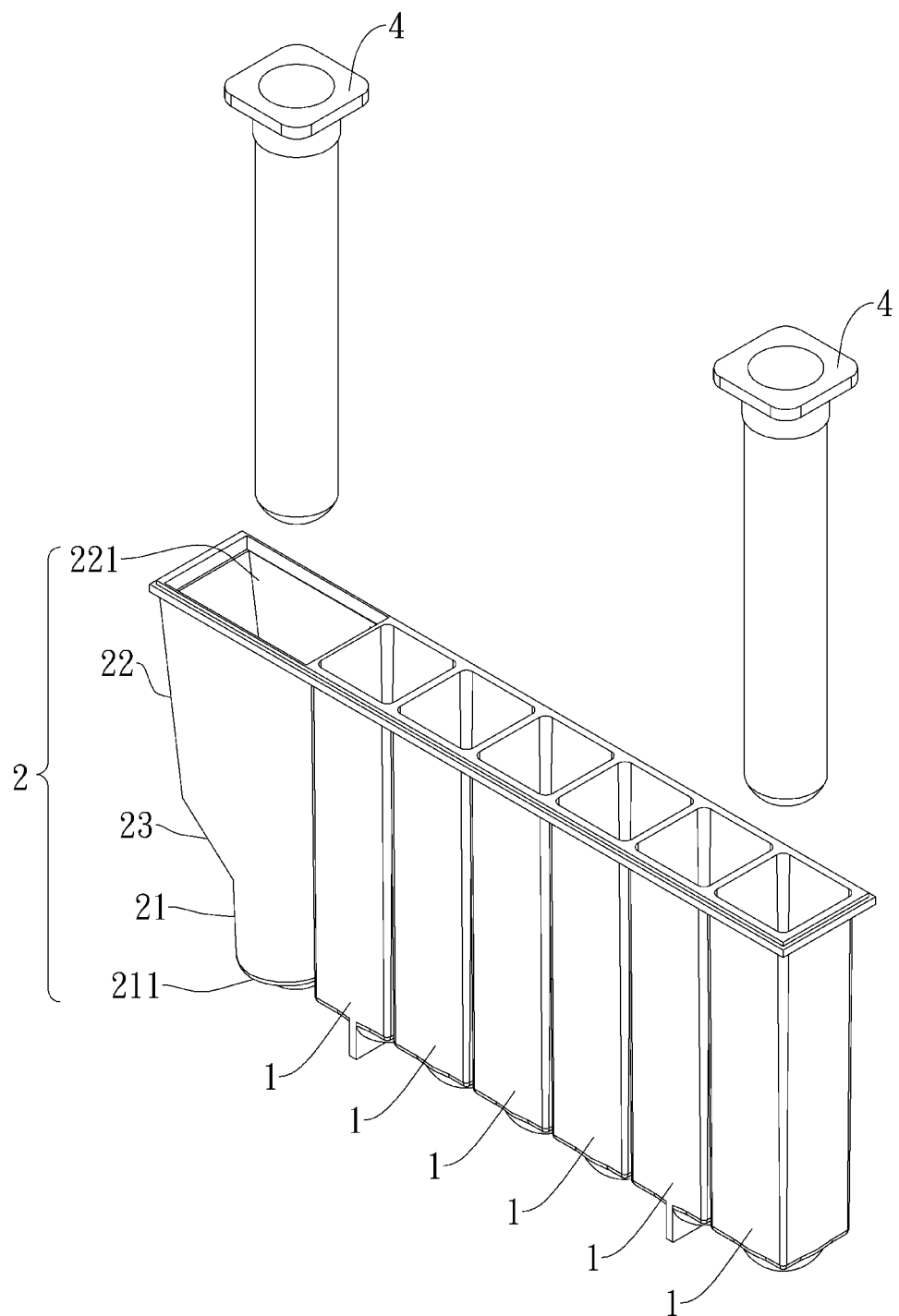
FIG. 5 illustrates an exploded pictorial drawing of a kit for a reagent vessel according to one embodiment of the present invention.
Figure 6:
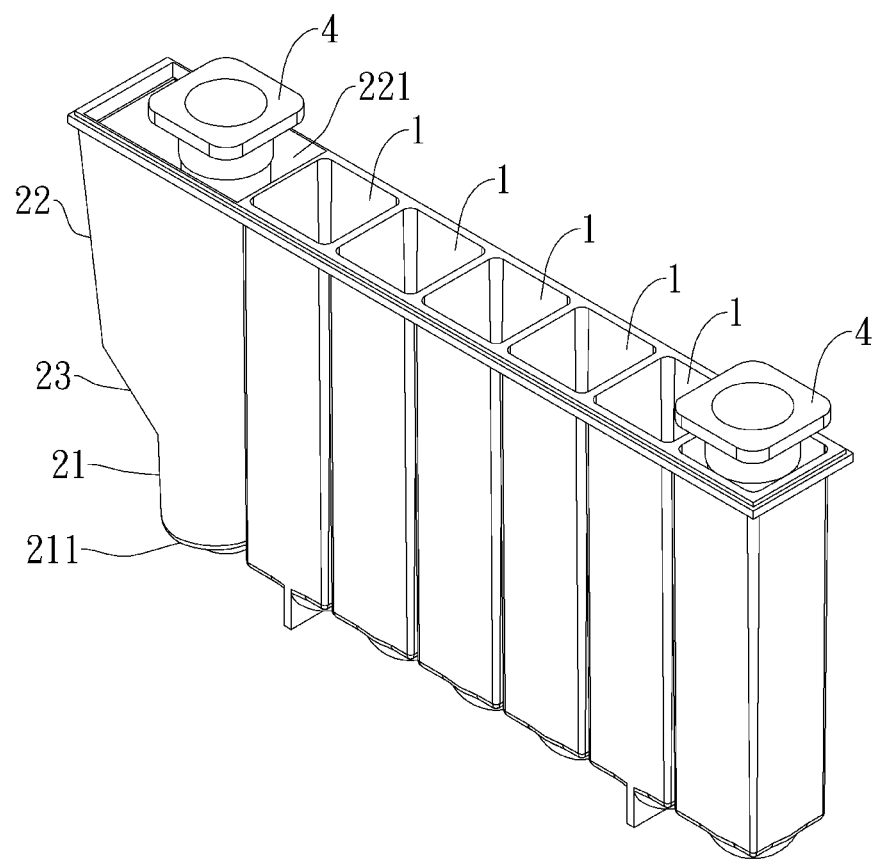
FIG. 6 illustrates a pictorial drawing of a kit for a reagent vessel according to one embodiment of the present invention.

Another example of the present invention was shown in the exploded pictorial drawing of FIG. 5 and the pictorial drawing of FIG. 6, providing a kit for a reagent vessel comprising: a reagent vessel and a stirrer jacket 4.

The first tubes 1 and the second tube 2 of the reagent vessel are used to contain a stirrer jacket for a stirring step. All elements are roughly the same as the above-mentioned example and will not be repeated here.

The stirrer jacket 4 covers the outside of the magnetic bar of a magnetic control device (not shown) correspondingly. Moreover, the bottom 211 of the second tube 2 and the stirrer jacket 4 forms a section area ratio value of about 1.1 to about 3.5. Preferably, the section area ratio value is about 1.1 to about 2.5.

When the kit uses, for example, in some operating steps for nucleic acids purification, a stirrer jacket 4 can be put on a stirrer jacket rack of the magnetic control device (not shown). When using the magnetic control device for cell lysis, the stirrer jacket rack is driven to move up and down, such that the stirrer jacket 4 will be extended into the second tube 2. Then, the stirrer jacket 4 will shift up and down quickly to flow the liquid in the second tube 2, and thus cells fully break in the lysis buffer to release nucleic acids or proteins. While magnetic beads absorption, the stirrer jacket rack is driven to move to one first tube 1 and shift up and down quickly to scatter magnetic beads herein. Then, the magnetic bar of the magnetic control device (not shown) moves down, inserting into the stirrer jacket rack, and thus magnetic beads will be adsorbed to the outside wall in front of the stirrer jacket rack 4 via the magnetic force.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A reagent vessel, comprising:
   at least one first tube and at least one second tube arranged adjacent to the first tube, wherein the second tube further comprises:
   a bottom section, comprising a bottom with a bottom section area in the end of the bottom section;
   an opening section, comprising an opening with an opening section area in the top of the opening section, wherein the opening section area is in a shape of a square and the bottom section area is in a shape of a circle, wherein the opening section area is greater than the bottom section area, and a section area ratio of the bottom section area to the opening section area is about 1:3.0; and a connecting section, being located between the bottom section and the opening section and having an inclined wall with an inclined angle of less than 50° with respect to a vertical plane.

2. The reagent vessel of claim 1, wherein the inclined angle is less than 45°.

3. The reagent vessel of claim 1, wherein the first tube or the second tube is used for containing magnetic beads, and at least one sample or reagent, and a stirrer jacket is further contained in the second tube for stirring the magnetic beads and at least one sample or reagent.

4. The reagent vessel of claim 1, which comprises a plurality of first tubes.

5. The reagent vessel of claim 4, wherein the first tubes are arranged in a line.

6. The reagent vessel of claim 1, which comprises a plurality of second tubes.

7. The reagent vessel of claim 6, wherein the second tubes are arranged adjacently.

8. The reagent vessel of claim 1, which further comprises a base comprising at least one containing tank for containing the reagent vessel.

9. The reagent vessel of claim 8, wherein the base comprises a plurality of containing tanks arranged side by side.

10. The reagent vessel of claim 9, wherein the number of containing tanks corresponds to the number of the reagent vessels.

11. A kit for a reagent vessel, comprising:
at least one stirrer jacket with a stirrer jacket section area; and
the reagent vessel of claim 1, wherein the second tube has a section area ratio value of the bottom section area to the stirrer jacket section area being about 1.1:1 to about 3.5:1.

12. The reagent vessel of claim 11, wherein the section area ratio value of the bottom section area to the stirrer jacket section area is about 1.1:1 to about 2.5:1.

* * * * *